United States Patent
Lee et al.

(10) Patent No.: US 10,675,091 B2
(45) Date of Patent: ***Jun. 9, 2020

(54) MICROWAVE ANTENNA HAVING A COAXIAL CABLE WITH AN ADJUSTABLE OUTER CONDUCTOR CONFIGURATION

(71) Applicant: COVIDIEN LP, Mansfield, MA (US)

(72) Inventors: Anthony C. Lee, Los Altos Hills, CA (US); Kenlyn S. Bonn, Lakewood, CO (US)

(73) Assignee: COVIDIEN LP, Mansfield, MA (US)

( * ) Notice: Subject to any disclaimer, the term of this patent is extended or adjusted under 35 U.S.C. 154(b) by 327 days.

This patent is subject to a terminal disclaimer.

(21) Appl. No.: 15/665,661

(22) Filed: Aug. 1, 2017

(65) Prior Publication Data

US 2017/0325887 A1 Nov. 16, 2017

Related U.S. Application Data

(63) Continuation of application No. 14/519,459, filed on Oct. 21, 2014, now Pat. No. 9,724,158, which is a
(Continued)

(51) Int. Cl.
*A61B 18/18* (2006.01)
*A61B 18/00* (2006.01)

(52) U.S. Cl.
CPC ..... *A61B 18/1815* (2013.01); *A61B 2018/00023* (2013.01); *A61B 2018/00077* (2013.01);
(Continued)

(58) Field of Classification Search
CPC ...... A61B 18/1815; A61B 2018/00023; A61B 2018/00077; A61B 2018/00214; A61B 2018/00577; A61B 2018/1861
See application file for complete search history.

(56) References Cited

U.S. PATENT DOCUMENTS

| D223,367 S | 4/1972 | Kountz |
| 3,820,118 A | 6/1974 | Hall |

(Continued)

FOREIGN PATENT DOCUMENTS

| CN | 1103807 C | 3/2003 |
| CN | 101283926 A | 10/2008 |

(Continued)

OTHER PUBLICATIONS

Search Report EP 06025700.3 dated Apr. 12, 2007.
(Continued)

*Primary Examiner* — Daniel W Fowler (57) ABSTRACT

A microwave ablation system includes a power source. A microwave antenna is adapted to connect to the power source via a coaxial cable that includes inner and outer conductors having a compressible dielectric operably disposed therebetween. The inner conductor in operative communication with a radiating section associated with the microwave antenna. The outer conductor includes a distal end transitionable with respect to each of the inner conductor, compressible dielectric and radiating section from an initial condition wherein the distal end has a first diameter to a subsequent condition wherein the distal end has second diameter. Transition of the distal end from the initial condition to the subsequent condition enhances the delivery of microwave energy from the power source to the inner conductor and radiating section such that a desired effect to tissue is achieved.

16 Claims, 6 Drawing Sheets

Related U.S. Application Data continuation of application No. 13/206,075, filed on Aug. 9, 2011, now Pat. No. 8,870,860.

(52) U.S. Cl.
CPC .............. *A61B 2018/00214* (2013.01); *A61B 2018/00577* (2013.01); *A61B 2018/1861* (2013.01)

(56) References Cited

U.S. PATENT DOCUMENTS

| | | |
|---|---|---|
| D263,020 S | 2/1982 | Rau, III |
| D266,842 S | 11/1982 | Villers et al. |
| 4,484,586 A | 11/1984 | McMickle et al. |
| D278,306 S | 4/1985 | McIntosh |
| D295,893 S | 5/1988 | Sharkany et al. |
| D295,894 S | 5/1988 | Sharkany et al. |
| 4,840,186 A | 6/1989 | Lekholm et al. |
| 5,150,717 A | 9/1992 | Rosen et al. |
| D354,218 S | 1/1995 | Van de Peer |
| 5,591,142 A | 1/1997 | Van Erp |
| 5,658,264 A | 8/1997 | Samson |
| 5,702,433 A | 12/1997 | Taylor et al. |
| 5,776,176 A | 7/1998 | Rudie |
| 5,882,333 A | 3/1999 | Schaer et al. |
| D424,693 S | 5/2000 | Pruter |
| D424,694 S | 5/2000 | Tetzlaff et al. |
| D425,201 S | 5/2000 | Tetzlaff et al. |
| 6,213,995 B1 | 4/2001 | Steen et al. |
| 6,277,083 B1 | 8/2001 | Eggers et al. |
| 6,287,302 B1 | 9/2001 | Berube |
| D449,886 S | 10/2001 | Tetzlaff et al. |
| 6,366,818 B1 | 4/2002 | Bolmsjo |
| D457,958 S | 5/2002 | Dycus et al. |
| D457,959 S | 5/2002 | Tetzlaff et al. |
| 6,496,736 B1 | 12/2002 | Carl et al. |
| D487,039 S | 2/2004 | Webster et al. |
| D496,997 S | 10/2004 | Dycus et al. |
| D499,181 S | 11/2004 | Dycus et al. |
| D525,361 S | 7/2006 | Hushka |
| 7,089,063 B2 | 8/2006 | Lesh et al. |
| D531,311 S | 10/2006 | Guerra et al. |
| D533,942 S | 12/2006 | Kerr et al. |
| D535,027 S | 1/2007 | James et al. |
| D541,418 S | 4/2007 | Schechter et al. |
| D541,938 S | 5/2007 | Kerr et al. |
| D564,662 S | 3/2008 | Moses et al. |
| D576,932 S | 9/2008 | Strehler |
| D594,736 S | 6/2009 | Esjunin |
| D594,737 S | 6/2009 | Kelly et al. |
| D606,203 S | 12/2009 | Husheer et al. |
| D613,412 S | 4/2010 | DeCarlo |
| D634,010 S | 3/2011 | DeCarlo |
| 8,870,860 B2 | 10/2014 | Lee et al. |
| 9,724,158 B2 | 8/2017 | Lee et al. |
| 2002/0058978 A1 | 5/2002 | Sass |
| 2007/0233057 A1 | 10/2007 | Konishi |
| 2008/0015517 A1 | 1/2008 | Geistert et al. |
| 2008/0161762 A1 | 7/2008 | Stehr et al. |
| 2008/0266203 A1 | 10/2008 | Rossetto et al. |
| 2009/0248005 A1 | 10/2009 | Rusin et al. |
| 2010/0094272 A1 | 4/2010 | Rossetto et al. |
| 2010/0217257 A1 | 8/2010 | Howat et al. |
| 2010/0234839 A1 | 9/2010 | Smith et al. |
| 2011/0056069 A1 | 3/2011 | Bonn |

FOREIGN PATENT DOCUMENTS

| | | |
|---|---|---|
| DE | 390937 C | 3/1924 |
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| EP | 246350 A1 | 11/1987 |
| EP | 0521264 A2 | 1/1993 |
| EP | 556705 A1 | 8/1993 |
| EP | 0558429 A1 | 9/1993 |
| EP | 0648515 A1 | 4/1995 |
| EP | 836868 A2 | 4/1998 |
| EP | 882955 A1 | 12/1998 |
| EP | 1159926 A3 | 3/2003 |
| EP | 1 905 375 A1 | 4/2008 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 55106 | 1/1993 |
| JP | 0540112 | 2/1993 |
| JP | 06343644 A | 12/1994 |
| JP | 07265328 A | 10/1995 |
| JP | 08056955 A | 3/1996 |
| JP | 08252263 A | 10/1996 |
| JP | 09000492 A | 1/1997 |
| JP | 09010223 A | 1/1997 |
| JP | 11244298 A | 9/1999 |
| JP | 2000342599 A | 12/2000 |
| JP | 2000350732 A | 12/2000 |
| JP | 20018944 | 1/2001 |
| JP | 2001003776 A | 1/2001 |
| JP | 200129356 | 2/2001 |
| JP | 200137775 A | 2/2001 |
| JP | 2001128990 A | 5/2001 |
| JP | 2001231870 A | 8/2001 |
| JP | 2008142467 A | 6/2008 |
| SU | 166452 | 1/1965 |
| SU | 401367 A1 | 10/1973 |
| SU | 727201 A2 | 4/1980 |
| WO | 2010035831 A1 | 4/2010 |

(56) References Cited

FOREIGN PATENT DOCUMENTS

OTHER PUBLICATIONS

Search Report EP 07000885.9 dated May 15, 2007.
Search Report EP 07001480.8 dated Apr. 19, 2007.
Search Report EP 07001481.6 dated May 2, 2007.
Search Report EP 07001485.7 dated May 23, 2007.
Search Report EP 07001488.1 dated Jun. 5, 2007.
Search Report EP 07001489.9 dated Dec. 20, 2007.
Search Report EP 07001491 dated Jun. 6, 2007.
Search Report EP 07001527.6 dated May 18, 2007.
European Search Report EP 07007783.9 dated Aug. 2007.
European Search Report EP 07008207.8 dated Sep. 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001016.8 dated Jan. 4, 2008.
European Search Report EP 08001019 dated Sep. 23, 2008.
European Search Report EP 08004974.5 dated Apr. 6, 2011.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08007924.7 partial dated Aug. 17, 2010.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09012389.4 dated Jul. 6, 2010.
European Search Report EP 09151621 dated Jun. 18, 2009.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Dumey et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure.TM." Diseases of the Colon & Rectum, vol. 46, No. 1, Jan. 2003.
Cosman et al., "Methods of Making Nervous System Lesions" in William RH, Rengachary SS (eds): Neurosurgery, New York: McGraw. cndot.Hill, vol. 111, (1984), pp. 2490-2499.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure. TM. Vessel Sealing System: A Case Report" Innovations That Work, Feb. 2002.
Humphries Jr. et al., "Finite-Element Codes to Model Electrical Heating and Non-Linear Thermal Transport in Thological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.

(56) References Cited

OTHER PUBLICATIONS

Jarrett et al., "Use of the LigaSure.TM. Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure.TM. Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSure.TM. Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure.TM. System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure.TM. Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M.A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.
Organ, L W., "Electrophysiologic Principles of Radiofrequency Lesion Making" Appl. Neurophysiol, vol. 39: pp. 69-76 (1976/1977).
European Search Report dated Feb. 24, 2015, corresopnding to European Application No. 12821976.3; 4 pages.
Humphries Jr. et al., "Finite-Element Codes to Model Electrical Heating and Non-Linear Thermal Transport in Biological Media", Proc. ASME HTD-355, 131 (1997).
English translation of Chinese Office Action and Search Report, dated Oct. 10, 2015, corresponding to Chinese Application No. 201280033854.9; 7 pages.
Search Report EP 04710258 dated Oct. 15, 2004.
Search Report EP 04752343.6 dated Jul. 31, 2007.
Search Report EP 04778192.7 dated Jul. 1, 2009.
Search Report EP 05002027.0 dated May 12, 2005.
Search Report EP 05002769.7 dated Jun. 19, 2006.
Search Report EP 05013463.4 dated Oct. 7, 2005.
Search Report EP 05013895 dated Oct. 21, 2005.
Search Report EP 05014156.3 dated Jan. 4, 2006.
Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 060205818 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
Search Report EP 09156861.8 dated Aug. 4, 2009.
Search Report EP 09161502.1 dated Sep. 2, 2009.
Search Report EP 09161502.1 extended dated Oct. 30, 2009.
Search Report EP 09165976.3 extended dated Mar. 17, 2010.
Search Report EP 09166708 dated Oct. 15, 2009.
Search Report EP 09166708.9 dated Mar. 18, 2010.
Search Report EP 09169376.2 extended dated Dec. 16, 2009.
Search Report EP 09172188.6 extended dated Apr. 23, 2010.
Search Report EP 09172838.6 extended dated Jan. 20, 2010.
European Search Report EP 09173268.5 extended dated Jan. 27, 2010.
European Search Report EP 09704429.1 extended dated Mar. 23, 2011.
European Search Report EP 10001767.2 extended dated Jun. 18, 2010.
European Search Report EP 10004950.1 extended dated Jul. 2, 2010.

(56) References Cited

OTHER PUBLICATIONS

European Search Report EP 10004951.9 extended dated Jul. 2, 2010.
European Search Report EP 10005533.4 extended dated Sep. 24, 2010.
European Search Report EP 10005534.2 extended dated Sep. 17, 2010.
European Search Report EP 10006373.4 extended dated Nov. 11, 2010.
European Search Report EP 10008139.7 extended dated Nov. 30, 2010.
European Search Report EP 10008140.5 extended dated Dec. 28, 2010.
European Search Report EP 10008533.1 extended dated Dec. 20, 2010.
European Search Report EP 10008850.9 extended dated Nov. 30, 2010.
European Search Report EP 10009731.0 extended dated Jan. 28, 2011.
European Search Report EP 10009732.8 extended dated Jan. 26, 2011.
European Search Report EP 10010943.8 extended dated Feb. 1, 2011.
European Search Report EP 10011750.6 extended dated Feb. 1, 2011.
European Search Report EP 10014042.5 extended dated Feb. 18, 2011.
European Search Report EP 10014080.5 extended dated Mar. 17, 2011.
European Search Report EP 10014081.3 extended dated Mar. 17, 2011.
European Search Report EP 10014705.7 extended dated Apr. 27, 2011.
European Search Report EP 10158944.8 extended dated Jun. 21, 2010.
European Search Report EP 10161596.1 extended dated Jul. 28, 2010.
European Search Report EP 10161722.3 extended dated Jun. 16, 2010.
European Search Report EP 10163235.4 dated Aug. 10, 2010.
European Search Report EP 10172634.7 dated Nov. 9, 2010.
European Search Report EP 10185413.1 dated Dec. 7, 2010.
European Search Report EP 10185413.1 dated Mar. 14, 2011.
European Search Report EP 10191321.8 dated Apr. 7, 2011.
European Search Report EP 11000548.5 extended dated Apr. 14, 2011.
European Search Report EP 11004942 dated Sep. 23, 2011.
European Search Report EP 11174318.3 dated Nov. 7, 2011.
International Search Report PCT/US97/05066 dated Jun. 24, 1997.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report and Written Opinion corresponding to PCT/US2012/050149, dated Jan. 2, 2013 (6 pages).
U.S. Appl. No. 08/136,098, filed Oct. 14, 1993, Roger A. Stern.
U.S. Appl. No. 08/483,742, filed Jun. 7, 1995, Roger A. Stern.
U.S. Appl. No. 12/861,333, filed Aug. 23, 2010, Joseph D. Brannan.
U.S. Appl. No. 12/944,951, filed Nov. 12, 2010, Joseph D. Brannan.
U.S. Appl. No. 12/977,390, filed Dec. 23, 2010, Joseph D. Brannan.
U.S. Appl. No. 12/977,415, filed Dec. 23, 2010, Joseph D. Brannan.
U.S. Appl. No. 12/985,124, filed Jan. 5, 2011, Joseph D. Brannan.
U.S. Appl. No. 12/985,136, filed Jan. 5, 2011, Joseph D. Brannan.
U.S. Appl. No. 12/985,155, filed Jan. 5, 2011, Joseph D. Brannan.
U.S. Appl. No. 12/985,179, filed Jan. 5, 2011, Joseph D. Brannan.
U.S. Appl. No. 13/020,562, filed Feb. 3, 2011, Joseph D. Brannan.
U.S. Appl. No. 13/020,664, filed Feb. 3, 2011, Kenlyn S. Bonn.
U.S. Appl. No. 13/024,041, filed Feb. 9, 2011, Joseph D. Brannan.
U.S. Appl. No. 13/029,521, filed Feb. 17, 2011, Joseph D. Brannan.
U.S. Appl. No. 13/029,594, filed Feb. 17, 2011, Joseph D. Brannan.
U.S. Appl. No. 13/043,665, filed Mar. 9, 2011, Richard A. Willyard.
U.S. Appl. No. 13/043,694, filed Mar. 9, 2011, Richard A. Willyard.
U.S. Appl. No. 13/050,729, filed Mar. 17, 2011, Casey M. Ladtkow.
U.S. Appl. No. 13/083,185, filed Apr. 8, 2011, Arnold V. DeCarlo.
U.S. Appl. No. 13/083,256, filed Apr. 8, 2011, Joseph D. Brannan.
U.S. Appl. No. 13/113,736, filed May 23, 2011, Ladtkow et al.
U.S. Appl. No. 13/118,929, filed May 31, 2011, Bonn et al.
U.S. Appl. No. 13/206,075, filed Aug. 9, 2011, Lee et al.
U.S. Appl. No. 13/236,997, filed Sep. 20, 2011, Behnke II, et al.
U.S. Appl. No. 13/237,068, filed Sep. 20, 2011, Behnke II, et al.
U.S. Appl. No. 13/237,187, filed Sep. 20, 2011, Behnke II, et al.
U.S. Appl. No. 13/237,342, filed Sep. 20, 2011, Behnke II, et al.
U.S. Appl. No. 13/237,488, filed Sep. 20, 2011, Behnke II, et al.
U.S. Appl. No. 13/267,369, filed Oct. 6, 2011, Prakash et al.
U.S. Appl. No. 13/268,143, filed Oct. 7, 2011, Kenlyn S. Bonn.
U.S. Appl. No. 13/281,605, filed Oct. 26, 2011, Prakash et al.
U.S. Appl. No. 13/290,462, filed Nov. 7, 2011, Kenlyn S. Bonn.
U.S. Appl. No. 13/298,461, filed Nov. 17, 2011, Buysse et al.
U.S. Appl. No. 13/344,753, filed Jan. 6, 2012, Lee et al.
U.S. Appl. No. 13/343,788, filed Jan. 5, 2012, William O. Reid, Jr.
U.S. Appl. No. 13/343,798, filed Jan. 5, 2012, William O. Reid, Jr.
U.S. Appl. No. 13/344,790, filed Jan. 6, 2012, Lee et al.
U.S. Appl. No. 13/351,463, filed Jan. 17, 2012, Smith et al.
U.S. Appl. No. 13/351,553, filed Jan. 17, 2012, Mahajan et al.
U.S. Appl. No. 13/358,129, filed Jan. 25, 2012, Joseph D. Brannan.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product Instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.TM. Breast Lesion Needle/Wire Localizer, Namic.RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure.TM. Vessel Sealing System and LigaSure.TM. Atlas 20 cm Open Instrument" Innovations That Work, Jun. 2003.
Muller et al., "Extended Left Hemicolectomy Using the LigaSure.TM. Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences.cndot.Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.

(56) References Cited

OTHER PUBLICATIONS

Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001)71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
Urologix, Inc.—Medical Professionals: Targis.TM. Technology (Date Unknown). "Overcoming the Challenge" located at: <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure.TM. Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.

MICROWAVE ANTENNA HAVING A COAXIAL CABLE WITH AN ADJUSTABLE OUTER CONDUCTOR CONFIGURATION

CROSS-REFERENCE TO RELATED APPLICATIONS

The present application is a continuation application of U.S. patent application Ser. No. 14/519,459, filed on Oct. 21, 2014, which is a continuation application of U.S. patent application Ser. No. 13/206,075, filed on Aug. 9, 2011 (now U.S. Pat. No. 8,870,860), the entire contents of which are incorporated by reference herein.

BACKGROUND

Technical Field

The present disclosure relates to microwave antennas. More particularly, the present disclosure relates to microwave antennas having a coaxial cable with an adjustable outer conductor configuration.

Background of Related Art

Microwave ablation procedures, e.g., such as those performed for menorrhagia, are typically done to ablate the targeted tissue to denature or kill the tissue. Many procedures and types of devices utilizing electromagnetic radiation therapy are known in the art. Such microwave therapy is typically used in the treatment of tissue and organs such as the prostate, heart, and liver.

One non-invasive procedure generally involves the treatment of tissue (e.g., a tumor) underlying the skin via the use of microwave energy. The microwave energy is able to non-invasively penetrate the skin to reach the underlying tissue. Typically, microwave energy is generated by a power source, e.g., microwave generator, and transmitted to tissue via a microwave antenna that is fed with a coaxial cable that operably couples to a radiating section of the microwave antenna.

To enhance energy delivery efficiency from the microwave generator to the microwave antenna, impedance associated with the coaxial cable, the radiating section and/or tissue need to equal to one another, i.e., an impedance match between the coaxial cable, the radiating section and/or tissue. In certain instances, an impedance mismatch may be present between the coaxial cable, the radiating section and/or tissue, and the energy delivery efficiency from the microwave generator to the microwave antenna is compromised, e.g., decreased, which, in turn, may compromise a desired effect to tissue, e.g., ablation to tissue.

SUMMARY

The present disclosure provides a microwave ablation system. The microwave ablation system includes a power source. A microwave antenna is adapted to connect to the power source via a coaxial cable that includes inner and outer conductors having a compressible dielectric operably disposed therebetween. The inner conductor in operative communication with a radiating section associated with the microwave antenna. The outer conductor includes a distal end transitionable with respect to each of the inner conductor, compressible dielectric and radiating section from an initial condition wherein the distal end has a first diameter to a subsequent condition wherein the distal end has second diameter. Transition of the distal end from the initial condition to the subsequent condition enhances the delivery of microwave energy from the power source to the inner conductor and radiating section such that a desired effect to tissue is achieved.

The present disclosure provides a microwave antenna adapted to connect to a power source for performing a microwave ablation procedure. The microwave antenna includes inner and outer conductors having a compressible dielectric operably disposed therebetween. The inner conductor in operative communication with a radiating section associated with the microwave antenna. The outer conductor includes a distal end transitionable with respect to each of the inner conductor, compressible dielectric and radiating section from an initial condition wherein the distal end has a first diameter to a subsequent condition wherein the distal end has second diameter. Transition of the distal end from the initial condition to the subsequent condition enhances delivery of microwave energy from the power source to the inner conductor and radiating section such that a desired effect to tissue is achieved.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Embodiments of the presently disclosed system and method are described in detail with reference to the drawing figures wherein like reference numerals identify similar or identical elements. As used herein and as is traditional, the term "distal" refers to the portion which is furthest from the user and the term "proximal" refers to the portion that is closest to the user. In addition, terms such as "above", "below", "forward", "rearward", etc. refer to the orientation of the figures or the direction of components and are simply used for convenience of description.

Figure 1:
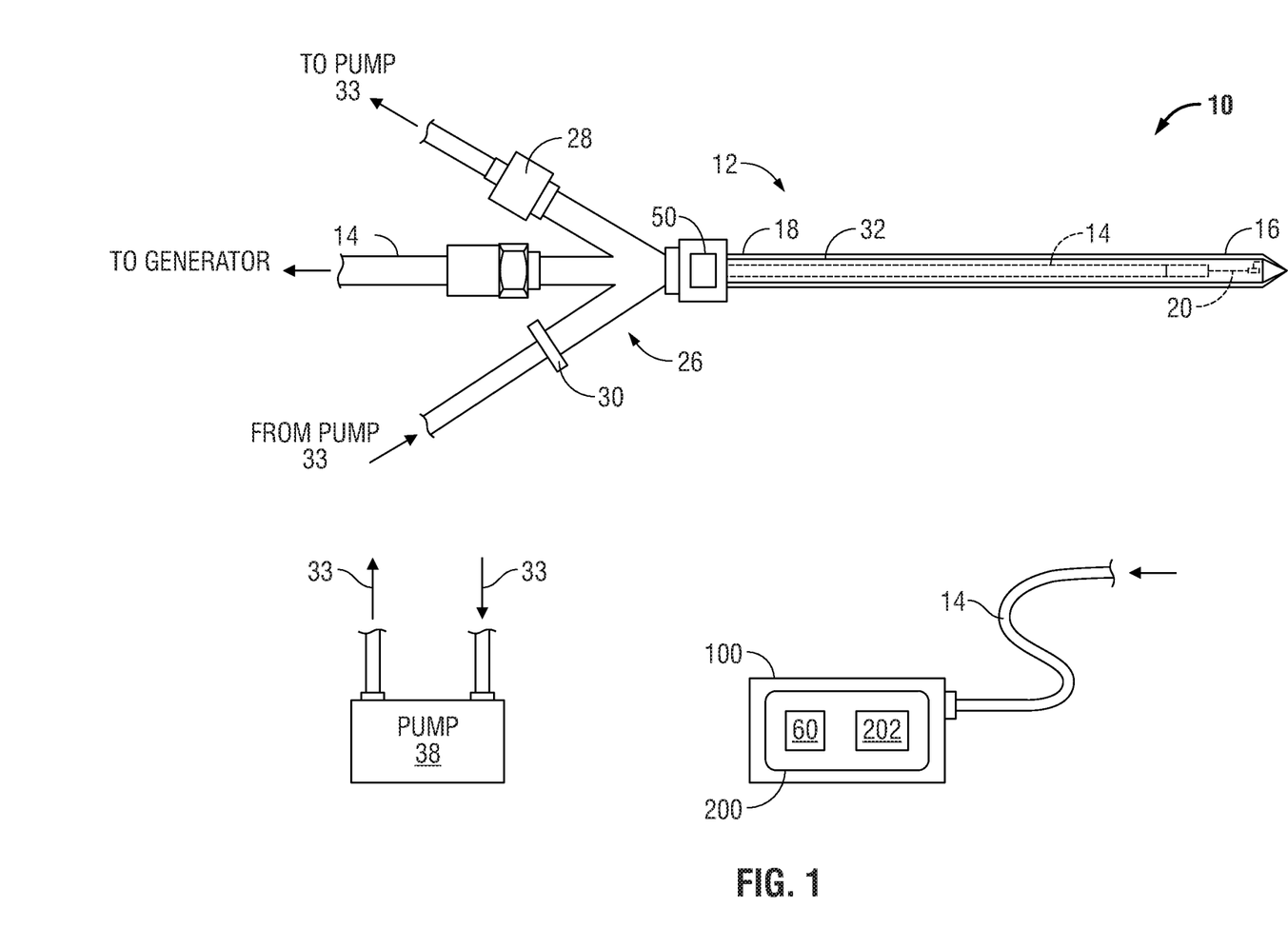
FIG. 1 is a schematic view of a microwave ablation system adapted for use with a microwave antenna that utilizes a coaxial cable with an adjustable outer conductor configuration according to an embodiment of the present disclosure.
Figure 2A:
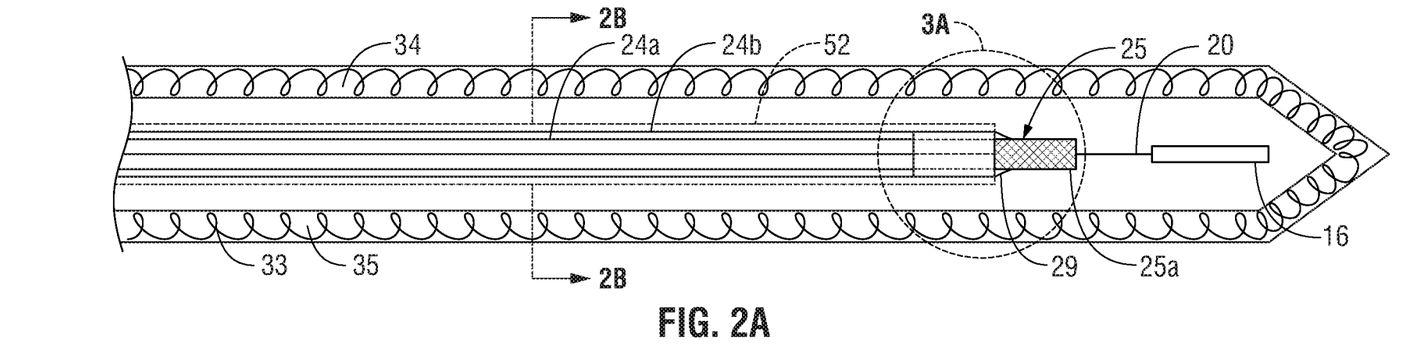
FIG. 2A is partial, cut-away view of a distal tip of the microwave antenna depicted in FIG. 1 illustrating the coaxial cable with the adjustable outer conductor configuration coupled to a radiating section associated with microwave antenna.
Figure 2B:
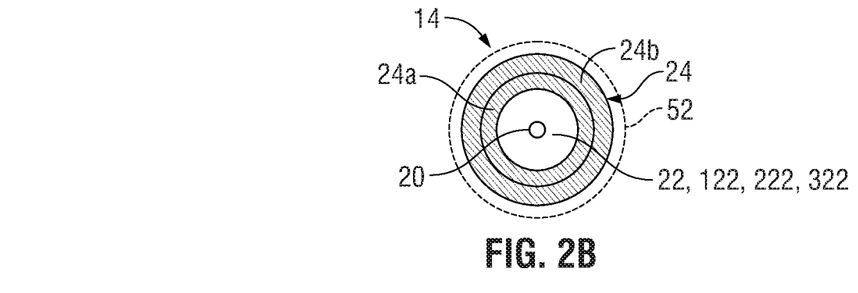
FIG. 2B is a cross-sectional view taken along line segment "2B-2B" illustrated in FIG. 2A.
Figure 2C:
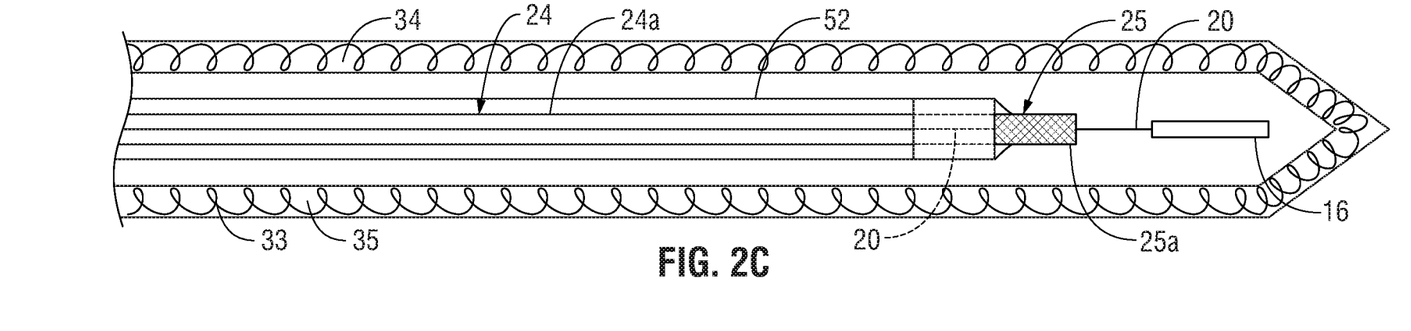
FIG. 2C is partial, cut-away view of an alternate distal tip design illustrating a coaxial cable with the adjustable outer conductor configuration coupled to a radiating section associated with microwave antenna according to an alternate embodiment of the present disclosure.

Referring now to FIGS. 1-2C, and initially with reference to FIG. 1, a microwave ablation system in accordance with an embodiment of the present disclosure is designated system 10. A microwave antenna 12 operably couples to generator 100 including a controller 200 that connects to the generator 100 via a flexible coaxial cable 14. In this instance, generator 100 is configured to provide microwave energy at an operational frequency from about 300 MHz to about 10 GHz. Microwave antenna 12 includes a distal radiating portion or section 16 that is connected by a feedline or shaft 18 to coaxial cable 14. Microwave antenna 12 couples to the cable 14 through a connection hub 26. The connection hub 26 includes an outlet fluid port 28 and an inlet fluid port 30 connected in fluid communication with a sheath or cannula 32. Cannula 32 is configured to circulate coolant fluid 33 from ports 28 and 30 around the antenna assembly 12 via respective fluid lumens 34 and 35 (FIG. 2A). Ports 28 and 30, in turn, couple to a supply pump 38. For a more detailed description of the microwave antenna 12 and operative components associated therewith, reference is made to commonly-owned U.S. Pat. No. 8,118,808, filed on Mar. 10, 2009, the entire contents of which are incorporated by reference herein.

With reference to FIGS. 2A-3B, and initially with reference to FIG. 2A, a coaxial cable 14 configuration according to an embodiment of the present disclosure is shown. Coaxial cable 14 extends from the proximal end of the microwave antenna 12 and includes an inner conductor 20 that is operably disposed within the shaft 18 and in electrical communication with a distal radiating section 16 (FIGS. 1 and 2A). Coaxial cable 14 includes a compressible dielectric 22 and an outer conductor 24 having an adjustable distal end 25 surrounding each of the inner conductor 20 and compressible dielectric 22. A portion of the coaxial cable 14 is movable in one or more directions to cause the distal end 25 to transition from a noncompressed condition to a compressed condition, described in greater detail below.

As noted above, an impedance mismatch may be present between a coaxial cable and a radiating section associated with conventional microwave antennas. As a result thereof, the energy delivery efficiency from the microwave generator to the microwave antenna may be compromised, e.g., decreased, which, in turn, may compromise a desired effect to tissue, e.g., tissue ablation. More particularly, impedance associated with the microwave antenna 12 varies over the course of an ablation cycle due to, for example, tissue complex permittivity changes caused by temperature increase. That is, because the ablated tissue is in a "near field" of the microwave antenna 12, the ablated tissue essentially becomes part of the microwave antenna 12. The impedance changes cause an increase in reflective power back to the generator 100 and reduce energy deposits into tissue.

In accordance with the present disclosure, a length of the coaxial cable 14 is configured for tuning (i.e., impedance matching) an impedance associated with the inner conductor 20, outer conductor 24 and tissue at a target tissue site such that an optimal transfer of electrosurgical energy is provided from the generator 100 to the radiating section 16 such that a desired tissue effect is achieved at a target tissue site. More particularly, the distal end 25 associated with the outer conductor 24 is adjustable, e.g., transitionable, adjacent an antenna feed point, i.e., adjacent the radiating section 16, to compress the compressible dielectric 22 and alter the ratio between the outer conductor 24 and the inner conductor 20, see FIG. 3A in combination with 3B.

Figure 3A:
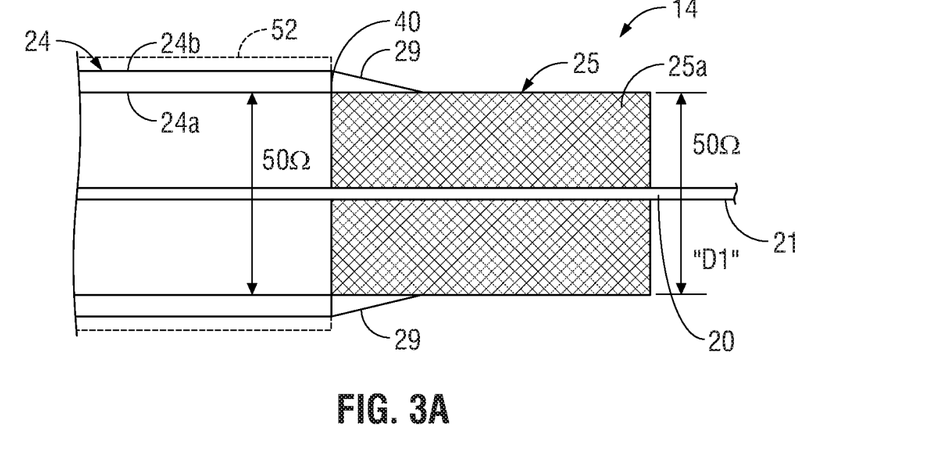
FIG. 3A is an enlarged view of the area of detail 3A depicted in FIG. 2A.
Figure 3B:
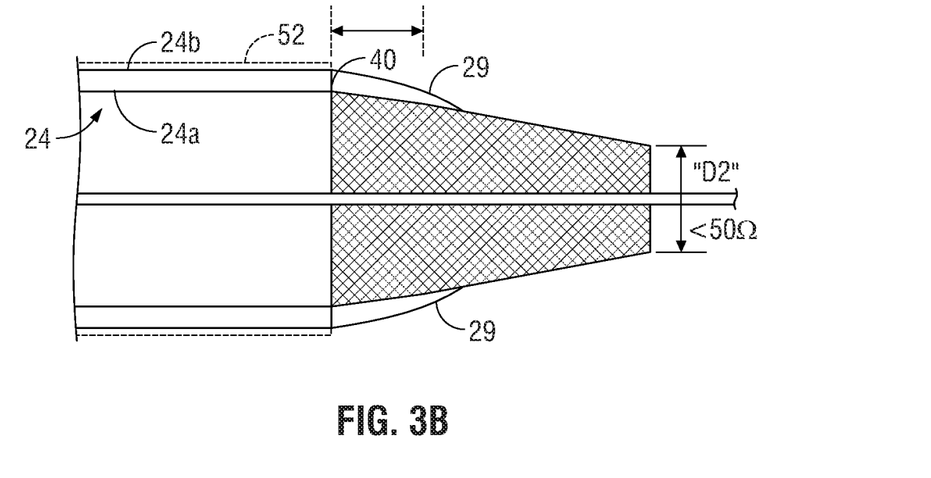
FIG. 3B is a side view of a coaxial cable depicted in FIG. 3A with a transitional distal end of an outer conductor shown in a compressed condition.

Referring to FIG. 3A, coaxial cable 14 includes inner conductor 20 that is configured similar to conventional inner conductors. More particularly, inner conductor 20 is made from one or more conductive materials, e.g., copper, and is substantially encased by a dielectric, e.g., compressible dielectric 22, see FIG. 2B, for example. A portion of the inner conductor 20 operably couples to the radiating section 16 by one or more suitable coupling methods. Inner conductor 20 serves as a conductive medium that transfers electrosurgical energy from the generator 100 to the radiating section 16. More particularly, a distal end 21 of the inner conductor extends past a feed point start (e.g., past outer conductor 24 and compressible dielectric 22, see FIG. 2C in combination with FIG. 3A) and couples to the radiating section 16 (see FIGS. 1 and 2A, for example). Typically, during initial transmission of electrosurgical energy from the generator 100 to the radiating section 16, the impedance present at the distal end 21 of the inner conductor 20 and the radiating section 16 is approximately equal to 50Ω (i.e., the characteristic impedance of the coaxial cable 14), as best seen in FIG. 3A. It should be noted that this 50Ω impedance is at least partially the result of the ratio of the diameter of the outer conductor 24 compared to the diameter of the inner conductor 20.

Compressible dielectric 22 is operably disposed between the outer conductor 24 and inner conductor 20 and, as noted above, substantially encases the inner conductor 20. Compressible dielectric 22 may be made from any suitable dielectric material that is capable of being deformed or compressed. Suitable material that compressible dielectric 22 may be made from includes but is not limited to electrical insulation paper, relatively soft plastics, rubber, etc. In certain embodiments, compressible dielectric 22 is made from polyethylene that has been chemically, or otherwise, treated to provide a degree of compressibility. In other instances, the compressible dielectric 22 may be made from polytetrafluoroethylene (PTFE), air, etc. Compressible dielectric 22 extends along a length of the coaxial cable 14. In the illustrated embodiment, compressible dielectric 22 extends partially along a portion of the coaxial cable 14 that is operably disposed within the microwave antenna 12. In certain embodiments, it may prove useful to provide the entire length of the coaxial cable with the compressible dielectric 22. Compressible dielectric 22 is deformable from an initially noncompressed condition to a compressed condition when the distal end 25 of the outer conductor 24 transitions from an initial, noncompressed, condition to a, subsequent, compressed condition; the significance of which is described in greater detail below. A distal end of the compressible dielectric 22 (the distal end of the compressible dielectric 22 is encased by the distal end 25 of the outer conductor and, as a result thereof, is not explicitly shown) defines a feed point start.

With continued reference to FIG. 3A, outer conductor 24 may be made from any suitable conductive material, e.g., a material having a generally rigid configuration, such as, for example, a pair of coaxially disposed circumferential sheets of copper. More particularly, outer conductor 24 includes a fixed outer conductor 24a and a movable or translatable outer conductor jacket or sleeve 24b ("outer sleeve 24b").

Fixed outer conductor 24a and outer sleeve 24b are disposed in electrical communication with one another. A portion, e.g., a distal end 40, of the fixed outer conductor 24a operably couples to the distal end 25. More particularly, distal end 40 of fixed outer conductor 24a is configured to support the distal end 25 such that the distal end 25 may transition from the noncompressed condition to the compressed condition. With this purpose in mind, the distal end 40 of the fixed outer conductor 24a may securely couple to the distal end 25 by one or more suitable coupling or securement methods. For example, in the illustrated embodiment, distal end 40 of fixed outer conductor 24a operably couples to the distal end 25 via one of soldering, welding and brazing. In certain embodiments, distal end 25 may be monolithically formed with the fixed outer conductor 24a. Fixed outer conductor 24a supports translatable outer sleeve 24b such that outer sleeve 24b may translate or rotate thereabout. In certain embodiments, one or more lubricious materials may be operably disposed between an external surface (not explicitly shown) of the fixed outer conductor 24a and an internal surface (not explicitly shown) of the outer sleeve 24b. For example, one or more suitable oils or waxes may be operably disposed between the external surface of the fixed outer conductor 24a and the internal surface of the outer sleeve 24b. Alternatively, or in combination therewith, one or both of the external surface of the fixed outer conductor 24a and the internal surface of the outer sleeve 24b may be made from a material that has a low coefficient of friction, e.g., a material such as, Delron, Torlon, PTFE, etc. Fixed outer conductor 24a is configured such that fixed outer conductor 24a remains in a substantially fixed orientation when the outer sleeve 24b is translated thereabout. Accordingly, when outer sleeve 24b is translated (or in some instances rotated) about fixed outer conductor 24a, outer sleeve 24b and fixed outer conductor 24a remain in electrical communication with one another.

Distal end 25 is transitionable with respect to each of the inner conductor 20, outer conductor 24 including fixed outer conductor 24a and outer sleeve 24b, compressible dielectric 22 and radiating section 16. More particularly, the distal end 25 transitions from an initial condition wherein the distal end 25 has a first diameter, to a subsequent condition wherein the distal end 25 has second diameter. That is, in a noncompressed condition, the distal end 25 includes a first diameter "D1" and when the distal end 25 is in a compressed condition the distal end 25 includes a second diameter "D2," wherein the diameter "D2" is less than diameter "D1," see FIG. 3A in combination with FIG. 3B, for example.

In the embodiment illustrated in FIGS. 3A and 3B, distal end 25 is made from a conductive wire mesh or weave 25a that is made from one or more suitable conductive materials, e.g., a wire mesh or weave made from copper, silver, gold, stainless steel, titanium, nickel or combination thereof. Wire mesh 25a includes a generally cylindrical configuration when in a pre-transition condition and a generally frusto-conical configuration when in the post transition condition, as best seen in FIGS. 3A and 3B. The configuration of a wire mesh or weave 25a facilitates transitioning from one condition to another while providing structural integrity for the distal end 25. As noted above, the distal end 40 of the fixed outer conductor 24a operably couples to the distal end 25. Likewise, a portion of the wire mesh 25a operably couples to the outer sleeve 24b by one or more suitable coupling methods including but not limited to one or more mechanical interfaces (e.g., weaving a portion of the wire mesh with and/or into the outer sleeve 24b), one or more types of bonding agents (e.g., epoxy adhesives), or other suitable coupling method. In the illustrated embodiment, a pair of loose proximal ends 29 couple and/or form part of the wire mesh or weave 25a and operably couple to the outer sleeve 24b via a heat cure adhesive, soldering, brazing, welding, etc. Accordingly, when the outer sleeve 24b is moved, e.g., translated proximally, it "pulls" the proximal ends 29, which, in turn, causes the wire mesh 25a of the distal end 25 to transition or tighten to the compressed condition, which, in turn, causes the compressible dielectric 22 to deform or compress to the compressed condition such that the diameter of the distal end 25 transitions from diameter "D1" to diameter "D2."

In accordance with the present disclosure, transitioning of the distal end 25 from the noncompressed condition to the compressed condition maximizes delivery of microwave energy from the generator 100 to the inner conductor 22 and radiating section 16 such that a desired effect to tissue is achieved. To this end, outer sleeve 24b is translatable relative to the fixed outer conductor 24a. As noted above, outer sleeve 24b operably couples to the distal end 25 of the outer conductor 24 and is configured such that proximal translation of the outer sleeve 24b relative to the fixed inner conductor 24a causes the distal end 25 to transition from the initial, noncompressed, condition to the subsequent, compressed condition. In the illustrated embodiment, the distance that outer sleeve translates is equal to or corresponds to the decease of the diameter associated with the distal end 25. More particularly, for a given amount of translation of outer sleeve 24b the diameter of the distal end 24b will decrease (or in some instances increase) proportionately. For example, in certain embodiments, a 1:1 ratio between translation of the outer sleeve 25b and transition of the distal end 25 from the first diameter "D1" to the second diameter "D2" is utilized. That is, when the outer sleeve 24b translates 0.001 inches the second diameter "D2" of the distal end 25 decreases 0.001 inches from the original diameter "D1." The ratio may be altered to achieve a desired impedance, tissue effect, ablation zone shape, etc. One skilled in the art can appreciate that other ratios may be utilized when manufacturing and/or assembling the coaxial cable 14.

A drive mechanism 50 is in electrical communication with generator 100 via an electric circuit 60 (FIG. 1) and operably couples to outer sleeve 24b. More particularly, drive mechanism 50 is operably disposed within microwave antenna 12 adjacent hub 26. Drive mechanism 50 includes one or more components (e.g., a drive rod, servo, servo drives, or other suitable device(s)) that are operably coupled to the outer sleeve 24b and configured to translate the outer sleeve 24b proximally and, in some instances, distally. In certain instances, drive mechanism 50 includes one or more components (e.g., a drive rod, servo, servo drives, or other suitable device(s)) that are operably coupled to the outer sleeve 24b and configured to rotate the outer sleeve 24b, e.g., rotate the outer sleeve 24b in a clockwise and/or counter-clockwise direction.

An outer plastic jacket or sheath 52 is operably disposed along a length of the coaxial cable 14. Sheath 52 functions similar to known sheaths that are typically associated with coaxial cables and, as such, only those features that are unique to sheath 52 are described hereinafter. One or more of the lubricious materials described above may be operably disposed between an internal surface of the sheath 52 and the external surface of the fixed outer conductor 24a and/or outer sleeve 24b.

In certain instances, sheath 52 (FIG. 2C) may operably couple to the distal end 25 and may be configured to "pull" the wire mesh 25a of the distal end 25. More particularly, and in this instance, the outer conductor 24 includes a fixed conductor 24a and does not include an outer sleeve 24b. That is, the sheath 52 takes the place of the outer sleeve 24b. More particularly, the sheath 52 encases the fixed outer conductor 24a and is operably coupled to and in operative communication with the drive mechanism 50 via the one or more of the previously described components.

In certain instances, one or more springs (not shown) may be operably associated with the wire mesh 25a of the distal end 25. In this instance, the spring(s) may be configured to facilitate transitioning the wire mesh 25a. For example, in some instances, it may prove useful or necessary to increase the impedance between the inner conductor 20 and distal end 25 of the outer conductor 24. In this instance, the outer sleeve 24b may be configured for distal translation relative to the fixed outer conductor 24a. That is, the outer sleeve 24b may be configured to translate distally past the distal end 40 of the fixed outer conductor 24a and toward the distal end 25 and/or radiating section 16 such that the wire mesh 25a transitions from an unexpanded condition to an expanded condition and the impedance between the inner conductor 20 and distal end 25 of the outer conductor 24 is increased. In this instance, the drive mechanism 50, and operative components associated therewith, is configured to translate the outer sleeve 24b (or in some instances, the sheath 52) distally.

In one particular embodiment, the controller 200 is configured to automatically control operation of the operative components associated with the coaxial cable 14. More particularly, when the impedance of the microwave antenna 12 requires adjustment, one or more modules, e.g., coaxial adjustment control module 202 (FIG. 1), associated with the controller 200 commands electric circuit 60 to supply power to the drive mechanism 50 such that the outer sleeve 24b may be actuated. In one particular embodiment, the controller 200 may be configured to determine a difference between forward and reflected power and determine a load mismatch thereby causing electric circuit to activate the drive mechanism 50.

Operation of system 10 is now described. A portion of the microwave antenna, e.g., a radiating section 16, is positioned adjacent a target tissue site. Initially, the diameter of the wire mesh 25a is approximately equal to "D1" that corresponds to an initial characteristic impedance "ZO" of the coaxial cable 14, e.g., an impedance "ZO" that is approximately equal to 50Ω. Thereafter, electrosurgical energy is transmitted from the generator 100 to the radiating section 16 of the microwave antenna 12 such that a desired tissue effect may be achieved at the target tissue site. As the radiating portion 16 emits electromagnetic energy into tissue and the tissue desiccates, an impedance mismatch between the microwave antenna 12 and tissue may be present at the target tissue site. To compensate for this impedance mismatch, the outer sleeve 24b (or in certain instances, the sheath 52) is "pulled" proximally. The compressible dielectric 22 allows the wire mesh 25a of the distal end 25 to transition, e.g., compress or tighten, under the pulling force provided by the outer sleeve 24b. The wire mesh 25a of the distal end 25 will to compress to a diameter that is approximately equal to "D2," which, in turn, decreases the impedance and compensates for the impedance mismatch. In accordance with the present disclosure, the configuration of adjustable distal end 25 of the fixed outer conductor 24a and inner conductor 20 improves electrosurgical energy transfer from the generator 100 to the microwave antenna 12 and/or the target tissue site and allows the microwave antenna 12 or portion associated therewith, e.g., radiating section 16, to be utilized with more invasive ablation procedures.

Figure 4A:
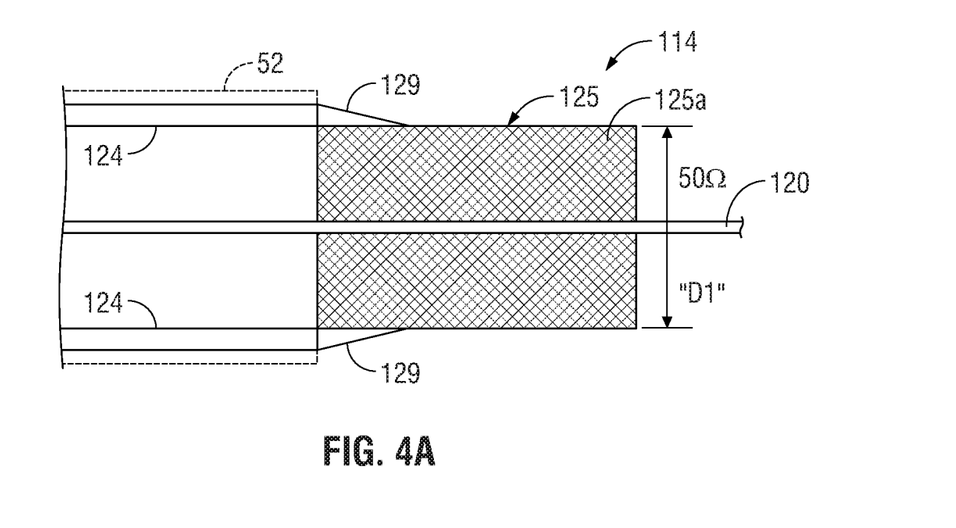
FIGS. 4A-4B are side views of an alternate embodiment of the coaxial cable depicted in FIGS. 3A and 3B with a transitional distal end of an outer conductor shown in noncompressed and compressed conditions, respectively.
Figure 4B:
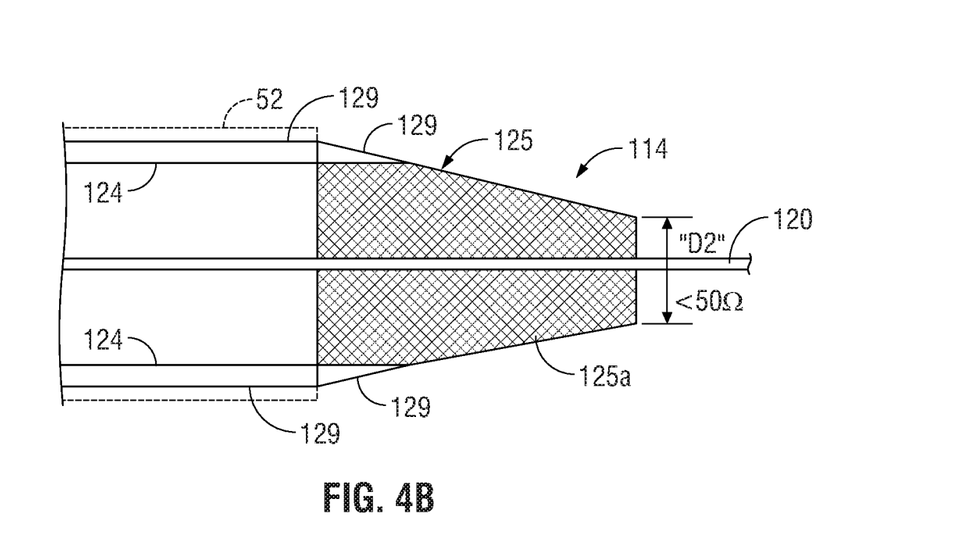

With reference to FIGS. 4A and 4B an alternate embodiment of the coaxial cable 14 is shown designated 114. Coaxial cable 114 is substantially similar to that of coaxial cable 14. As a result thereof, only those features that are unique to coaxial cable 114 are described in detail.

Coaxial cable includes an inner conductor 120, an outer conductor 124 and a compressible dielectric 122 that surrounds the inner conductor 120. A distal end 125 operably couples to a distal end 140 of the outer conductor 124 and is made from one or more suitable types of a shape memory alloy (e.g., Nitinol) that forms a wire mesh 125a. More particularly, shape memory alloys (SMAs) are a family of alloys having anthropomorphic qualities of memory and trainability and are particularly well suited for use with medical instruments. Nitinol which can retain shape memories for two different physical configurations and changes shape as a function of temperature. SMAs undergo a crystalline phase transition upon applied temperature and/or stress variations. A particularly useful attribute of SMAs is that after it is deformed by temperature/stress, it can completely recover its original shape on being returned to the original temperature. The ability of an alloy to possess shape memory is a result of the fact that the alloy undergoes a reversible transformation from an austenite state to a martensite state with a change in temperature (or stress-induced condition). This transformation is referred to as a thermoelastic martensite transformation. Under normal conditions, the thermoelastic martensite transformation occurs over a temperature range which varies with the composition of the alloy, itself, and the type of thermal-mechanical processing by which it was manufactured. In other words, the temperature at which a shape is "memorized" by an SMA is a function of the temperature at which the martensite and austenite crystals form in that particular alloy.

Unlike the configuration of coaxial cable 14 depicted in FIGS. 3A and 3B, the mesh 125a does not rely on a "pulling" force to transition from a noncompressed condition to a compressed condition. More particularly, a pair of loose proximal ends 129 associated with the wire mesh 125 is in electrical communication with the generator 100 and/or one or more modules associated with the controller 200. In this instance, the generator, or an operative component associated therewith, e.g., electrical circuit 60, supplies current to the wire mesh 125a such that the wire mesh 125a may transition from a noncompressed condition, to a compressed condition, e.g., its original cold forged shape. More particularly, as current is supplied, via the proximal ends 129, to the wire mesh 125a, the current heats the wire mesh 125a and causes the wire mesh 125a to transition back to its (referring to the wire mesh 125a) cold forged shape, e.g., a distal end 125 having a generally frustoconical shape with a diameter approximately equal to "D2," see FIG. 4B, for example.

Operation of system 10 that includes a microwave antenna 12 with a coaxial cable 112 is now described. Only those operative features that are unique to the microwave antenna 12 with a coaxial cable 112 are described hereinafter.

To compensate for an impedance mismatch, electrical current is supplied to the wire mesh 125a such that current may resistively heat the wire mesh 125a. Resistively heating the wire mesh 125a causes the wire mesh 125a to transition back to the cold forged shape of the wire mesh 125a. The compressible dielectric 122 allows the wire mesh 125a of the distal end 25 to transition, e.g., compress or tighten, to a generally frustoconical shape with a diameter approximately equal to "D2," which, in turn, decreases the impedance and compensates for the impedance mismatch. In accordance with the present disclosure, the configuration of adjustable distal end 125 of the outer conductor 124 and inner conductor 120 improves electrosurgical energy transfer from the generator 100 to the microwave antenna 12 and/or the target tissue site and allows the microwave antenna 12 or portion associated therewith, e.g., radiating section 16, to be utilized with more invasive ablation procedures.

Figure 5A:
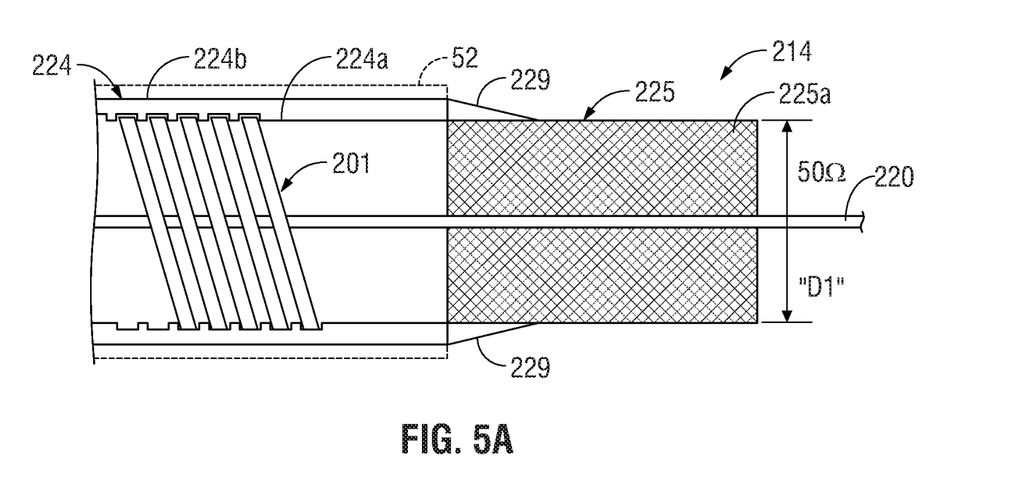
FIGS. 5A-5B are side views of an alternate embodiment of the coaxial cable depicted in FIGS. 3A and 3B with a transitional distal end of an outer conductor shown in noncompressed and compressed conditions, respectively.
Figure 5B:
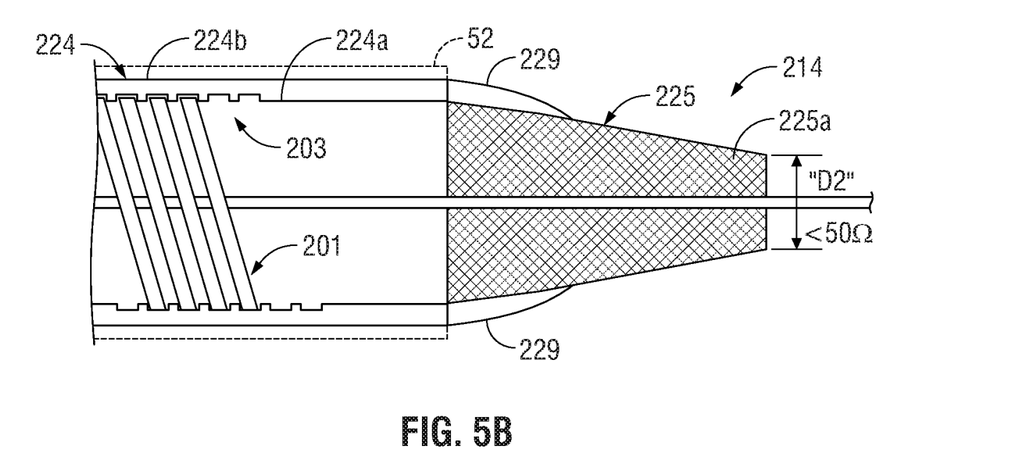

With reference to FIGS. 5A and 5B an alternate embodiment of the coaxial cable 14 is shown designated 214. Coaxial cable 214 is substantially similar to that of coaxial cable 14. As a result thereof, only those features that are unique to coaxial cable 214 are described in detail.

Coaxial cable includes an inner conductor 220, an outer conductor 224 that includes a fixed outer conductor 224a and a rotatable outer sleeve 224b, and a compressible dielectric 222 that surrounds the inner conductor 220. Outer sleeve 224b is rotatably coupled to the fixed internal outer conductor 224a and wire mesh 225a of distal end 225 such that rotation of the outer sleeve 224b causes wire mesh 225a to transition from a noncompressed condition to a compressed condition. In the embodiment illustrated in FIGS. 5A and 5B, the outer sleeve 224b is rotatably coupled to the fixed outer conductor 224a by one or more suitable mechanical interfaces. More particularly, one or more ramped threads 201 are in mechanical communication with one or more corresponding slots 203. For illustrative purposes, the ramped threads 201 are shown operably disposed along an exterior surface of the fixed outer conductor 224a and the corresponding slots 203 are shown operably disposed along an interior surface of the outer sleeve 224b. This configuration of ramped threads 201 and corresponding slots 203 ensures that clockwise rotation of the outer sleeve 224b causes proximal translation of the outer sleeve 224b, which, in turn, causes the wire mesh 225a to transition from a noncompressed condition to a compressed condition. Conversely, counterclockwise rotation of the outer sleeve 224b causes distal translation of the outer sleeve 224b, which, in turn, causes the wire mesh 225a to transition from the compressed condition back to the noncompressed condition. While the present disclosure describes a configuration of a ramped threads 201 and corresponding slots 203 to facilitate rotation of the outer sleeve 224b with respect to fixed outer conductor 224a, it is within the purview of the present disclosure that one or more other methods or devices may be utilized to achieve the intended purposes described herein.

Distal end 225 operably couples to a distal end 240 of the fixed outer conductor 224a in a manner as described above with respect to distal end 25 and distal end 24.

A pair of loose proximal ends 229 associated with the wire mesh 225 is operably coupled to the outer sleeve 224b such that rotation of outer sleeve 224b causes the wire mesh 225a to transition from a noncompressed condition, to a compressed condition. Proximal ends 229 may be coupled to the outer sleeve 224b by one or more suitable coupling methods, e.g., one or more coupling methods previously described above with respect to proximal ends 29.

A drive mechanism 50, configured in a manner as described above, is in operable communication with the outer sleeve 224b. More particularly, the drive mechanism 50 is configured to impart rotational motion of the outer sleeve 224b such that the outer sleeve 224b may translate proximally and, in some instances, distally.

To compensate for an impedance mismatch, the outer conductor (or in certain instances, the sheath 52) is rotated in a clockwise direction. The compressible dielectric 222 allows the wire mesh 225a of the distal end 225 to transition, e.g., compress or tighten, under the rotational or pulling force provided by the outer sleeve 224b. The wire mesh 225a of the distal end 225 will to compress to a diameter that is approximately equal to "D2," which, in turn, decreases the impedance and compensates for the impedance mismatch. In accordance with the present disclosure, the configuration of adjustable distal end 225 of the outer conductor 224 and inner conductor 220 improves electrosurgical energy transfer from the generator 100 to the microwave antenna 12 and/or the target tissue site and allows the microwave antenna 12 or portion associated therewith, e.g., radiating section 16, to be utilized with more invasive ablation procedures.

Figure 6A:
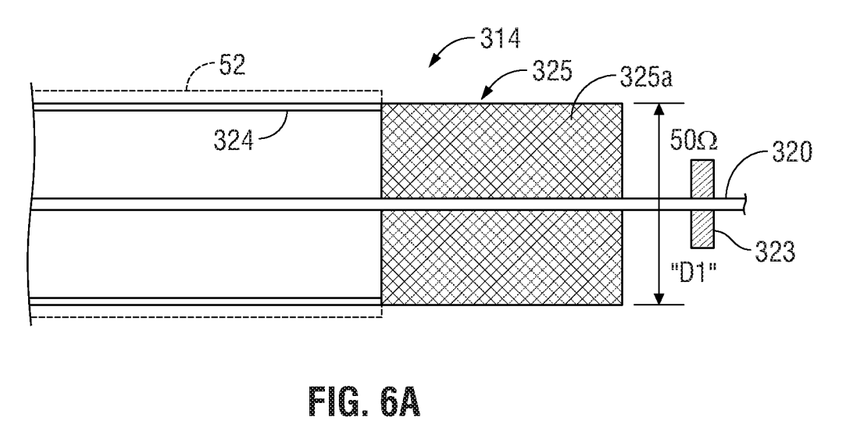
FIGS. 6A-6B are side views of yet another embodiment of the coaxial cable depicted in FIGS. 3A and 3B with a transitional distal end of an outer conductor shown in noncompressed and compressed conditions, respectively.
Figure 6B:
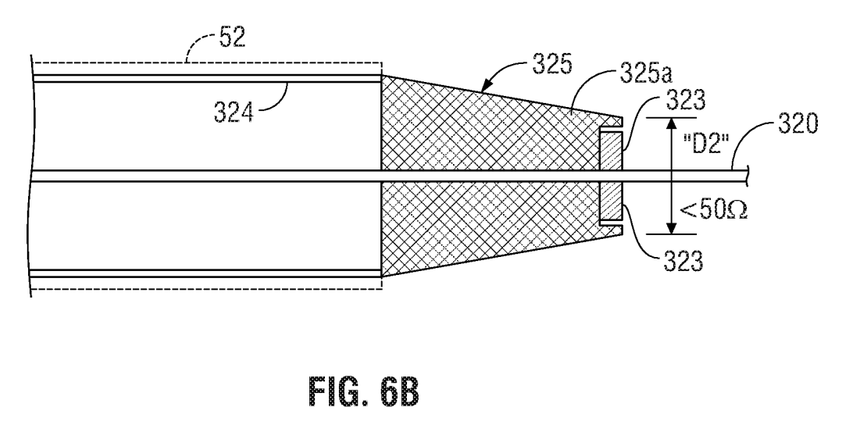

With reference to FIGS. 6A and 6B an alternate embodiment of the coaxial cable 14 is shown designated 314. Coaxial cable 314 is substantially similar to that of coaxial cable 14. As a result thereof, only those features that are unique to coaxial cable 314 are described in detail.

Coaxial cable includes a translatable inner conductor 320, an outer conductor 324 and a compressible dielectric 322 that surrounds the inner conductor 320. Unlike the inner conductors previously described, inner conductor 320 is configured to translate, e.g., proximally and/or distally, relative to the outer conductor 324 and compressible dielectric 322. To this end, one or more lubricious materials described above may be operably disposed between the compressible dielectric 322 and inner conductor 320 to facilitate translation of the inner conductor 320.

An incompressible dielectric disk 323 (disk 323) of suitable proportion and having a suitable shape is operably disposed on (e.g., via one or more suitable securement methods) and along a length of the inner conductor 320. Disk 323 is configured to "push" against a distal portion of the compressible dielectric 322 when the inner conductor 320 is translated proximally such that the compressible material is caused to compress or deform radially inward. To this end, disk 323 is of substantially rigid construction including a generally circumferential configuration having a diameter that is less than a predetermined diameter, e.g., diameter "D2," of a wire mesh 325a when the wire mesh 325a is in a compressed state. Disk 323 may be made from any suitable material including but not limited those previously described herein, e.g., polyethylene.

Compressible dielectric 322 may be configured in a manner as previously described, e.g., compressible dielectric 22. In the embodiment illustrated in FIGS. 6A and 6B, compressible dielectric 322 is operably coupled or secured to the wire mesh 325a by one or more suitable coupling or securement methods. More particularly, compressible dielectric 322 is secured to the wire mesh 325 via an epoxy adhesive. Accordingly, when the compressible dielectric 322 deforms or compresses, the wire mesh 325a transitions to the compressed condition.

A drive mechanism 50, configured in a manner as described above, is in operable communication with the inner conductor 320. More particularly, the drive mechanism 50 is configured to impart translation of the inner conductor 320 such that the inner conductor 320 may translate proximally and, in some instances, distally.

Outer conductor 324 includes a distal end 325 that operably couples to a distal end 340 that forms a wire mesh 325a.

To compensate for an impedance mismatch, inner conductor 320 including disk 323 is moved proximally relative to outer conductor 324 and compressible dielectric 322. The compressible dielectric 322 pushes against the wire mesh 325a of the distal end 325, this, in turn, causes the wire mesh 325a to transition, e.g., compress or tighten, under the pushing force against the compressible dielectric 322 provided by the disk 323 and inner conductor 320. The wire mesh 325a of the distal end 325 will to compress to a diameter that is approximately equal to "D2," which, in turn, decreases the impedance and compensates for the impedance mismatch.

From the foregoing and with reference to the various figure drawings, those skilled in the art will appreciate that certain modifications can also be made to the present disclosure without departing from the scope of the same. For example, one or more modules associated with the generator 100 and/or controller 200 may be configured to monitor the impedance at the target tissue site during the transmission of electrosurgical energy from the generator 100 to the microwave antenna 12. More particularly, one or more sensors (e.g., one or more voltage, impedance, current sensors, etc.) may be operably positioned at a predetermined location and adjacent the radiating section 16 and/or target tissue site. More particularly, the sensor(s) may be operably disposed along a length of the microwave antenna 12 and in operative communication with the module(s) associated with the generator 100 and/or controller 200. The sensor(s) may react to or detect impedance fluctuations associated with the microwave antenna 12 and/or tissue at the target tissue site during the ablation procedure. In this instance, the sensor(s) may be configured to trigger a control signal to the module(s) when an impedance mismatch is present. When the module(s) detects a control signal, the module calls for power to be supplied to an electrical circuit that is in operative communication with the drive mechanism 50 such that the drive mechanism 50 actuates one or more of the operative components, e.g., outer sleeve 24b, such that a respective wire mesh, e.g., wire mesh 25a of distal end 25, is caused to transition from the noncompressed condition to the compressed condition.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of treating tissue, comprising:
   transmitting microwave energy through a radiating section of a microwave antenna into tissue; and
   compressing a dielectric disposed between an inner conductor of the microwave antenna and an outer conductor of the microwave antenna to transition a portion of the outer conductor from a first configuration in which the portion of the outer conductor has a first diameter, to a second configuration in which the portion of the outer conductor has a second diameter that is less than the first diameter.

2. The method according to claim 1, wherein the outer conductor transitions from the first configuration to the second configuration via actuation of a drive mechanism operably coupled to the outer conductor.

3. The method according to claim 1, wherein compressing the dielectric decreases an impedance of the microwave antenna.

4. The method according to claim 3, wherein compressing the dielectric includes decreasing a thickness of the dielectric as the portion of the outer conductor transitions from the first configuration to the second configuration.

5. The method according to claim 1, further comprising longitudinally translating an outer sleeve of the outer conductor relative to a fixed segment of the outer conductor and an inner conductor of the microwave antenna causing the portion of the outer conductor to transition from the first configuration to the second configuration.

6. The method according to claim 1, wherein the portion of the outer conductor is transitioned until an impedance of the microwave antenna matches an impedance of the tissue.

7. The method according to claim 1, wherein the portion of the outer conductor is disposed at a distal section of the outer conductor, such that the portion of the outer conductor transitions between the first and second configurations relative to a proximal section of the outer conductor.

8. The method according to claim 1, wherein the portion of the outer conductor includes a wire mesh that is in an expanded state in the first configuration and a contracted state in the second configuration.

9. A method of treating tissue, comprising:
   transmitting electrosurgical energy through a radiating section of a microwave antenna into tissue;
   transitioning a portion of an outer conductor of the microwave antenna from a first configuration to a second configuration, thereby compressing a dielectric disposed between an inner conductor of the microwave antenna and the outer conductor, such that a thickness of the dielectric decreases.

10. The method according to claim 9, wherein the outer conductor transitions from the first configuration to the second configuration via actuation of a drive mechanism operably coupled to the outer conductor.

11. The method according to claim 9, wherein the dielectric is compressed until an impedance of the microwave antenna matches an impedance of the tissue.

12. The method according to claim 9, further comprising moving a sheath relative to the outer conductor to transition the outer conductor from the first configuration to the second configuration.

13. The method according to claim 9, further comprising moving the inner conductor relative to the outer conductor to transition the portion of the outer conductor from the first configuration to the second configuration.

14. The method according to claim 9, wherein the portion of the outer conductor is disposed at a distal section of the outer conductor, such that the portion of the outer conductor transitions between the first and second configurations relative to a proximal section of the outer conductor.

15. The method according to claim 9, wherein the portion of the outer conductor includes a wire mesh that is in an expanded state in the first configuration and a contracted state in the second configuration.

16. A method of treating tissue, comprising:
   transmitting microwave energy through a radiating section of a microwave antenna into tissue; and
   matching an impedance of the microwave antenna to an impedance of the tissue by transitioning a portion of an outer conductor of the microwave antenna from a first configuration in which the portion of the outer conductor has a first diameter, to a second configuration in which the portion of the outer conductor has a second diameter that is less than the first diameter.

* * * * *